(12) United States Patent
Ward et al.

(10) Patent No.: US 8,042,544 B2
(45) Date of Patent: Oct. 25, 2011

(54) PREVENTION OF VENTILATOR ASSOCIATED PNEUMONIA (VAP)

(75) Inventors: Kevin R. Ward, Glenn Allen, VA (US); Curtis N. Sessler, Richmond, VA (US); Mary Jo Grap, Midlothian, VA (US); Laurence J. Dinardo, Richmond, VA (US); Bruce D. Spiess, Manakin Sabot, VA (US); Rao R. Ivatury, Richmond, VA (US); Cindy Munro, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 1039 days.

(21) Appl. No.: 11/217,667

(22) Filed: Sep. 2, 2005

(65) Prior Publication Data
US 2006/0107962 A1 May 25, 2006

Related U.S. Application Data

(60) Provisional application No. 60/607,070, filed on Sep. 3, 2004.

(51) Int. Cl.
*A61M 16/00* (2006.01)
(52) U.S. Cl. .............. 128/207.14; 128/207.15
(58) Field of Classification Search ............ 128/204.18, 128/207.14, 207.15, 200.26, 207.17; 604/265, 604/11
See application file for complete search history.

(56) References Cited

U.S. PATENT DOCUMENTS

| | | | | |
|---|---|---|---|---|
| 518,810 A * | 4/1894 | Miles et al. | ................ | 277/533 |
| 3,481,339 A | 12/1969 | Millet | | |
| 3,638,655 A * | 2/1972 | Doherty | ............... | 128/207.15 |
| 4,976,261 A * | 12/1990 | Gluck et al. | ............. | 128/207.15 |
| 5,033,466 A * | 7/1991 | Weymuller, Jr. | ........ | 128/207.15 |
| 5,065,755 A * | 11/1991 | Klafta | ............... | 128/200.26 |
| 5,188,630 A * | 2/1993 | Christoudias | ................ | 606/1 |
| 5,230,332 A | 7/1993 | Strickland | | |
| 5,285,777 A * | 2/1994 | Beckwith | ............. | 128/207.15 |
| 5,364,358 A * | 11/1994 | Hewitt et al. | ............. | 604/99.01 |
| 5,370,656 A * | 12/1994 | Shevel | ............. | 606/196 |
| 5,501,215 A * | 3/1996 | Huerta | ............. | 128/207.15 |
| 5,524,642 A * | 6/1996 | Rosenblatt | ............. | 128/849 |
| 5,819,723 A * | 10/1998 | Joseph | ............. | 128/207.14 |
| 5,937,861 A * | 8/1999 | Augustine | ............. | 128/207.15 |
| 6,443,147 B1 * | 9/2002 | Matter | ............. | 128/200.26 |
| 6,745,773 B1 * | 6/2004 | Gobel | ............. | 128/207.15 |
| 7,258,120 B2 * | 8/2007 | Melker | ............. | 128/207.14 |
| 2004/0011358 A1 | 1/2004 | Smaldone et al. | | |
| 2004/0161447 A1 * | 8/2004 | Paul | ............. | 424/430 |
| 2004/0220534 A1 * | 11/2004 | Martens et al. | ............. | 604/265 |
| 2006/0140984 A1 * | 6/2006 | Tamarkin et al. | ............. | 424/400 |
| 2008/0011304 A1 * | 1/2008 | Stewart | ............. | 128/207.15 |

OTHER PUBLICATIONS

Seegobin R D, van Hasselt G L, Aspiration beyond endotracheal cuffs, Can Anaesth Soc J 1986;33(3 Pt 1):273-9.*

* cited by examiner

*Primary Examiner* — Danton DeMille
(74) *Attorney, Agent, or Firm* — Whitham Curtis Christofferson & Cook, PC

(57) ABSTRACT

Ventilator associated pneumonia (VAP) may be prevented in a patient, or its occurrence reduced in a population of patients, by disposing in a patient airway an anti-VAP device or an anti-VAP material. By reducing the problem of bacterial-containing secretions that otherwise build up in the airway of the intubated patient, VAP can be prevented from occurring in intubated patients, such as patients intubated with an endotracheal tube (ETT) or a nasogastric tube.

22 Claims, 18 Drawing Sheets

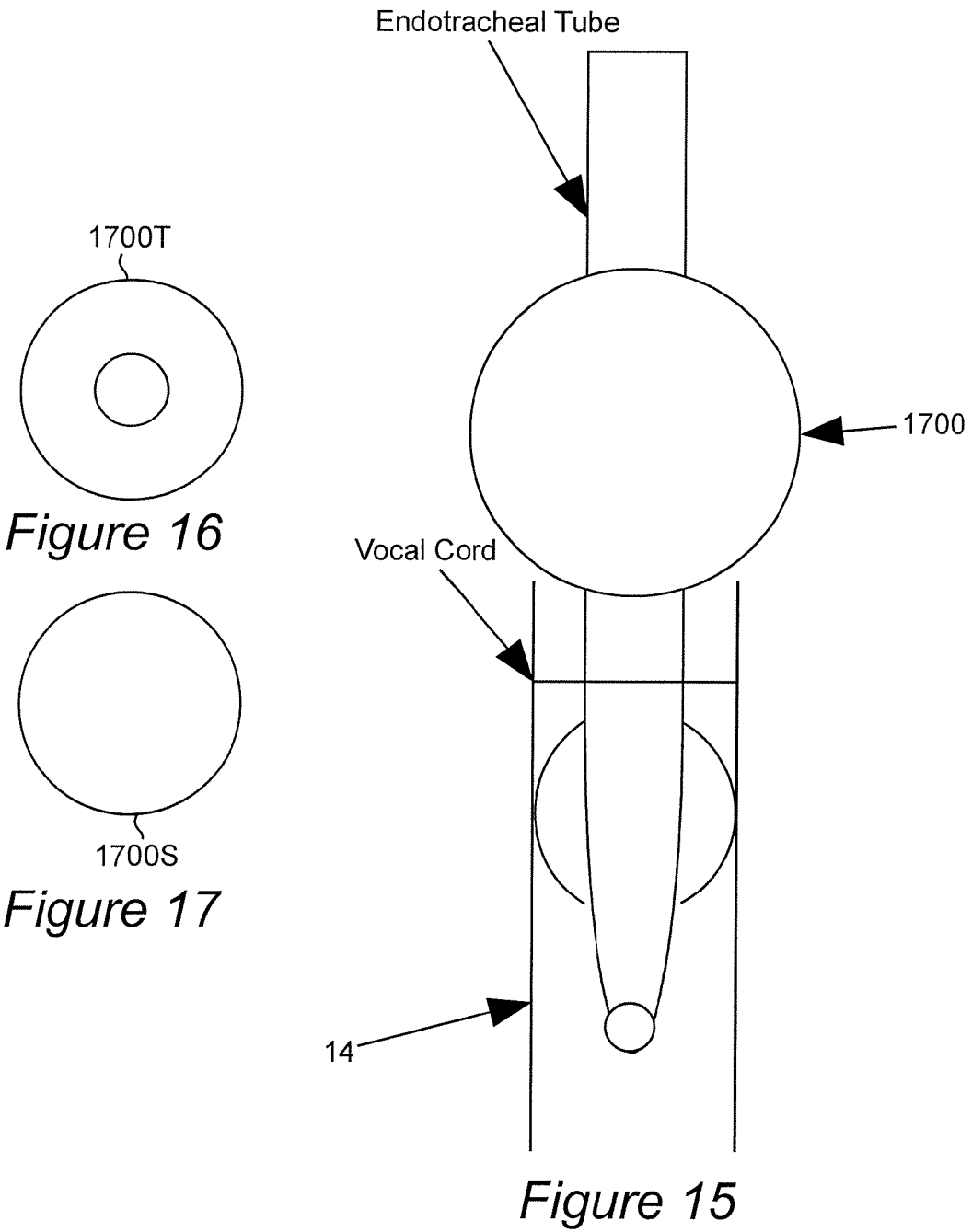

PREVENTION OF VENTILATOR ASSOCIATED PNEUMONIA (VAP)

RELATED APPLICATION

This application claims benefit of U.S. provisional application No. 60/607,070 filed Sep. 3, 2004 titled "Device and methods to prevent ventilator associated pneumonia and to provide laryngeal anesthesia during mechanical ventilation."

FIELD OF THE INVENTION

This invention relates to treatment of patients who are intubated with an endotracheal tube (ETT), and especially to ventilator associated pneumonia (VAP) undesirably associated with such intubation.

BACKGROUND OF THE INVENTION

Ventilator associated pneumonia (VAP) is a potentially preventable cause of pneumonia that occurs in patients who are endotracheally intubated and mechanically ventilated for more than 48 hours. VAP may occur in up to 65% of patients in the intensive care unit (ICU) and is associated with an increase in morbidity and mortality. It is estimated that cost of diagnosing and treating VAP exceeds 1.1 billion dollars annually. Young P J, Ridley S A, Ventilator-associated pneumonia, Diagnosis, pathogenesis and prevention, Anaesthesia 1999; 54(12):1183-97; Morehead R S, Pinto S J, Ventilator-associated pneumonia, Arch Intern Med 2000; 160(13):1926-36.

VAP is usually a bacterial nosocomial pneumonia, which was neither present nor incubating at the time of endotracheal intubation. Causes of VAP are multifactorial (FIG. 1). The diagnosis of VAP is difficult and expensive. Controversy continues to exists in the methodology in making a definitive diagnosis. Treatment is also controversial and the use of empiric antibiotics is believed to have contributed to making the overall treatment of true VAP more difficult. Patients developing VAP require additional testing to make the diagnosis and additional treatments. A major cost to the treatment is prolonging the time patients require mechanical ventilation and thus care in the ICU setting. This increased time of treatment in this setting is likely to actually increase the chances of additional complications including developing additional VAPs and antibiotic resistant organisms.

The microbiology of VAP consist of a combination of Gram positive, Gram negative, and anaerobic organisms, most of which are oropharyngeal or enteric in origin. As such a major mechanism believed to be responsible for the development of VAP is the microaspiration of pooled oropharyngeal secretions around the inflated cuff of an endotracheal tube (FIG. 2).

Despite the use of high volume low pressure (HVLP) endotracheal tube cuffs, there is clear evidence that small channels develop between the endotracheal tube cuff and the trachea, which allow passage of subglottic secretions into the lower respiratory tract. These channels develop because small folds develop from incomplete expansion of the endotracheal tube cuff. Seegobin R D, van Hasselt G L, Aspiration beyond endotracheal cuffs, Can Anaesth Soc J 1986; 33(3 Pt 1):273-9. The number of the folds or channels can be reduced if higher volumes are used to inflate the cuffs. However, higher volumes will result in higher pressures being created between the cuff and the tracheal mucosa thus placing the tracheal mucosa at risk for necrosis.

One strategy to reduce VAP from pooled secretions has been to perform continuous aspiration of subglottic secretions (CASS). A specially designed endotracheal tube called the HI-LO® EVAC tube by Mallinckrodt allows for this. This endotracheal tube contains a separate dorsal lumen ending in the subglottic space just above HVLP cuff. Fluid can be drained along this channel with suction. When clinically studied, the incidence of VAP has been reduced from 29% to 13% with intermittent drainage and 32% to 18% with continuous drainage. (Valles J, Artigas A, Rello J, Bonsoms N, Fontanals D, Blanch L, et al., Continuous aspiration of subglottic secretions in preventing ventilator-associated pneumonia, Ann Intern Med 1995; 122(3):179-86; Kollef M H, Skubas N J, Sundt T M, A randomized clinical trial of continuous aspiration of subglottic secretions in cardiac surgery patients, Chest 1999; 116(5):1339-46.) The method appears to result in major cost savings if its use were wide spread. (Shorr A F, O'Malley P G, Continuous Subglottic Suctioning for the Prevention of Ventilator-Associated Pneumonia: Potential Economic Implications, Chest 2001; 119:228-35.) The disadvantage of this method is that suction is required. Because endotracheal intubation occurs in many non-ICU areas, suction is not readily available. Patients are likely to be a most risk for aspiration from subglottic secretions very early after intubation especially when it is performed in less than ideal places such as on the wards, the emergency department, or in the prehospital setting. For example, over 55% of head-injured patients requiring intubation in the field or emergency department development pneumonia which might be from very early aspiration. (Livingston D H, Prevention of ventilator-associated pneumonia, Am J Surg 2000; 179(2A Suppl): 12S-17S.) Furthermore, patients often require movement from the ICU to other locations within the hospital in order to undergo additional treatments or diagnostic studies. Continuous suction may not be available during these times. In addition, maneuvers such as changing patient position in a bed may serve to increase balloon channel size or relationship between the HI-LO EVAC port and the pooled secretions thus creating additional opportunity for aspiration.

A number of methods, which involve changes in cuff design, have reported various degrees of success but none have undergone extensive clinical testing. One method has used a latex cuff, which appears to provide the sealing effectiveness of low volume high pressure cuffs without damage to the tracheal wall. (Young P J, Ridley S A, Downward G., Evaluation of a new design of tracheal tube cuff to prevent leakage of fluid to the lungs, Br J Anaesth 1998; 80(6):796-9.) The addition of keeping the cuff at a constant pressure using a special inflation system adds to the degree of protection. (Young P J, Basson C, Hamilton D, Ridley S A, Prevention of tracheal aspiration using the pressure-limited tracheal tube cuff, Anaesthesia 1999; 54(6):559-63.) A modification of this cuff using silicone has been studied in humans requiring tracheostomy and appears to decrease leakage of supraglottic fluid compared conventional HVLP cuffs. (Young P J, Burchett K, Harvey I, Blunt M C, The prevention of pulmonary aspiration with control of tracheal wall pressure using a silicone cuff, Anaesth Intensive Care 2000; 28(6):660-5.) This tube and cuff are manufactured by Euromedical Industries and have been used as part of the intubating laryngeal mask system.

Another cuff called the Portex Soft Seal HVLP cuff (Portex Ltd, Hythe UK) has been tested against other HVLP cuffs in bench models and appears to perform better in terms of reducing leakage around the cuff. (Young P J, Blunt M C, Compliance characteristics of the Portex Soft Seal Cuff improves seal against leakage of fluid in a pig trachea model, Crit Care (Lond) 1999; 3(5):123-26.)

Also a unique thin walled endotracheal tube has been designed in which a traditional air filled cuff is replaced by a series of circumferential gills. During intubation, the tube is placed so that a number of the gills are above and below the vocal cords. This creates a seal for positive pressure ventilation (up to 40 cm H$_2$O of peak inspiratory pressure) as well as a barrier to supraglottic secretions. (Reali-Forster C, Kolobow T, Giacomini M, Hayashi T, Horiba K, Ferrans V J, New ultrathin-walled endotracheal tube with a novel laryngeal seal design: Long-term evaluation in sheep, Anesthesiology 1996; 84(1): 162-72; discussion 27A.) Although tested in animals we are not aware of any clinical testing. It is unknown what type of reaction might be caused by the gills coming in contact with the vocal cords in terms of irritation.

Other device strategies to reduce or prevent VAP have been to embed the endotracheal tube with antimicrobials such as silver. This method appears to reduce the bacterial load. (Hartmann M, Guttmann J, Muller B, Hallmann T, Geiger K, Reduction of the bacterial load by the silver-coated endotracheal tube (SCET), a laboratory investigation, Technol Health Care 1999; 7(5):359-70) However, it is presumed that the secretions must be in contact with the silver for sufficient periods of time for its antimicrobial activity to be effective. In regards to this, intubation done in less than ideal circumstances where patients may be at greatest risk for microaspiration means that antibiotic embedded systems or tubes designed to prevent formation of biofilm might not be effective in this time early time range.

Another major problem in the patient requiring endotracheal intubation and mechanical ventilation is the need for sedation due to the coughing reflexes induced by contact of the endotracheal tube and cuff with points of the supra and subglottic portions of the larynx. These points include the epiglottis, vocal cords, and tracheal mucosa. These reflexes are capable of producing such irritation and coughing as to require significant systemic sedation. This degree of additional sedation can impede physical and neurologic assessment of the patient and delay efforts for weaning of mechanical ventilation. This is of great importance because additional time spent utilizing mechanical ventilation will necessarily result in the incurrence of significant expense and may potentially result in the development of VAP with all of its complications and additional expense.

Methods/devices used to reduce the coughing reflex associated with endotracheal tubes include instilling local anesthetics through the lumen of the endotracheal tube. This method is believed to anesthetize to carina of the tracheal-bronchial tree. One device was found on the internet, which depicts a multilumen endotracheal tube allowing for instillation of anesthetic agents such as lidocaine. These ports appear to end at various locations along the tracheal bronchial tree. It is assumed that intermittent administration and contact of anesthesia at these points will provide sufficient anesthesia of the tracheal bronchial tree in contact with the endotracheal tube as to significantly blunt the coughing reflex.

Patent literature about prevention and/or reduction of ventilator associated pneumonia is as follows.

U.S. Patent Application No. 20030073625 was published Apr. 17, 2003, by Redman et al., for "Methods of preventing ventilator associated pneumonia by oral administration of antimicrobial IB-367 peptides."

U.S. Patent Application No. 20040079376 was published Apr. 29, 2004, by Melker, for "Endotracheal tube apparatus and method for using the same to reduce the risk of infections." A tube-in-tube endotracheal tube apparatus is disclosed.

U.S. Patent Application No. 20050065141 was published Mar. 24, 2005, by Odlink et al., for "Carbapenems useful in treating and preventing pulmonary infections, pharmaceutical compositions thereof and modes of administration thereof."

Conventional strategies to reduce VAP necessitate purchase of a separate endotracheal tube, which making implementation difficult especially if VAP prevention strategies are to be performed in all settings at the earliest possible time. In addition, each conventional strategy is relatively singular or limited in its ability to prevent VAP.

SUMMARY OF THE INVENTION

The above problems and shortcomings have been addressed by the present invention. The present inventors have recognized that ventilator associated pneumonia (VAP) may be prevented in a patient (such as, e.g., a human patient, a veterinary patient), or its occurrence reduced in a population of patients, by using a relatively-simple anti-VAP device or an anti-VAP material in a space that otherwise would be where bacterial-containing secretions would form. By reducing the problem of bacterial-containing secretions that otherwise build up in the airway of the intubated patient, VAP can be prevented from occurring in intubated patients.

In one preferred embodiment, the invention provides an anti-VAP system, comprising an anti-VAP device or an anti-VAP material, wherein the device or the material is sized and configured to be disposed in a patient airway which is intubated with an endotracheal tube (ETT), such as, e.g., an anti-VAP system comprising a device attached or attachable to the ETT; an anti-VAP system wherein the device or the material is touching the ETT; an anti-VAP system wherein the device or the material is in proximity to the ETT; an anti-VAP system wherein the device or the material is situated within a distance of 1 cm or closer to where secretions build up in the airway of the intubated patient; an anti-VAP system comprising an anti-VAP attachment mechanically attachable to, and detachable from, the ETT; an anti-VAP system comprising a device that is a sponge or is spongy; an anti-VAP system comprising a foamable material; an anti-VAP system comprising a semisolid or a gel; an anti-VAP system wherein the device or the material remains in the patient airway for at least an hour; an anti-VAP system wherein the device or the material comprises at least one selected from the group consisting of: an absorbing agent; an antibacterial agent; and an anesthetic agent; an anti-VAP system wherein the device or the material is removable from the ETT separately without requiring removal of the ETT; an anti-VAP system comprising an anti-VAP attachment configured to receive an ETT through an elastic tubular member (such as, e.g., a tubular member made of latex, silicone; a tubular member coated or embedded with one or more of bacteriocidal agents, bacteriostatic agents, anesthetics, absorbing agents, and compounds inhibiting biofilm formation; etc.) that covers a balloon of the ETT and/or covers some portion of ETT distal and/or proximal sections; an anti-VAP system comprising an anti-VAP attachment that includes at least one port through which may be delivered antibacterial and/or anesthetic agents, and/or absorbing agents to the intubated patient; an anti-VAP system comprising an anti-VAP attachment that comprises a sleeve into which an ETT may be received, wherein a sleeved ETT fits through a patient's vocal cords and into the trachea and the sleeve spans the vocal cords; an anti-VAP system wherein an anti-VAP attachment is assembled onto an ETT. In another preferred embodiment, the invention provides a device or material that allows passage of a nasogastric tube (such as, e.g., a device that covers the nasogastric tube; an anti-VAP system that comprises an anti-VAP device or material that partially recedes into the upper esophagus; an anti-VAP system that comprises a device that is placeable as part of the nasogastric tube (such as, e.g., a device that is placeable after placement of the nasogastric tube; etc.); etc.

In another preferred embodiment, the invention provides a method of preventing ventilator associated pneumonia (VAP) in a patient (such as, e.g., a human patient, a veterinary patient) needing endotracheally intubation, comprising: disposing an anti-VAP device or an anti-VAP material in a region where secretions otherwise build up in the airway of the patient when intubated (such as, e.g., a disposing step that comprises attaching an anti-VAP attachment to an endotracheal tube; a disposing step that comprises placing an anti-VAP sponge or spongy material touching or near the ETT; a disposing step that comprises foaming an anti-VAP foamable material on or near the ETT; a disposing step that comprises providing an anti-VAP material (such as a gel, a powder, a liquid, etc.) on or near the ETT; etc.), including, e.g., methods wherein the disposing step is performed while the ETT is in the airway of the patient; methods wherein the disposing step is performed with the ETT outside the airway of the patient; methods wherein the patient does not incur symptoms of bacterial nosocomial pneumonia; methods wherein the patient does not incur symptoms of Gram positive, Gram negative or anaerobic VAP organisms; methods further including a step of providing airway anesthesia; In another preferred embodiment, the invention provides a device or material that allows passage of a nasogastric tube (such as, e.g., a device that covers the nasogastric tube; methods which use an anti-VAP device that allows passage of a nasogastric tube (such as an anti-VAP device that is placeable as part of the nasogastric tube; a device that is placeable after placement of the nasogastric tube; etc.); etc.

The invention in another preferred embodiment provides a method of reducing occurrence of ventilator associated pneumonia (VAP) in a population of patients endotracheally intubated, comprising: for each patient, disposing an anti-VAP device or an anti-VAP material in a region where secretions otherwise build up in the airway of the patient when intubated (such as disposing performed before patient intubation; disposing performed after patient intubation; disposing performed a mixture of before and after patient intubation), such as, e.g., methods comprising attaching an anti-VAP attachment to an endotracheal tube; methods wherein microaspiration is reduced; methods wherein oropharyngeal bacterial load is reduced; etc.

Another preferred embodiment of the invention provides a method of preventing ventilator associated pneumonia (VAP) in a patient (such as, e.g., a human patient, a veterinary patient) needing endotracheally intubation, comprising: disposing a space-occupying anti-VAP device or a space-occupying anti-VAP material in a mouth and/or oropharynx of a patient when intubated, wherein the anti-VAP device or anti-VAP material remains disposed therein during a period of intubation of the patient, and wherein the anti-VAP device or anti-VAP material is other than an endotracheal tube (ETT), such as methods in which silver embedded material (such as ribbons, pads, etc.) are disposed in an oropharynx of an ETT-intubated patient.

A further preferred embodiment of the invention provides a method of reducing or preventing colonization of the respiratory tract with gastrointestinal organisms, such as by, e.g., a device or material that partially recedes into the upper esophagus, whereby colonization of the respiratory tract with gastrointestinal organisms is reduced or prevented; etc.

In another preferred embodiment, the invention provides a method of preventing ventilator associated infection (such as, e.g., VAP) in a patient (such as, e.g., a human patient, a veterinary patient) needing intubation (such as, e.g., endotracheal intubation, nasogastric intubation), comprising: a) within an intubated patient, non-surgically disposing a controllably-removable space-occupying anti-infection device or a space-occupying anti-infection material in an open space where otherwise infection-causing organisms would accumulate, and wherein the anti-infection device or anti-infection material is other than an endotracheal tube (ETT) or a nasogastric tube; b) removing the anti-infection device or anti-infection material from the intubated patient. In such methods there may be further provided a step c) of subsequently re-occupying the open space where otherwise infection-causing organisms would accumulate in the intubated patient with an anti-infection device or anti-infection material.

The invention in a further preferred embodiment provides an anti-VAP system, comprising an anti-VAP device or an anti-VAP material, wherein the device or the material is sized and configured to be disposed in a patient airway intubated with a nasogastric tube.

Another preferred embodiment of the invention provides a method of reducing occurrence of ventilator associated pneumonia (VAP) in a patient whose esophagus is intubated with a nasogastric tube, comprising: disposing an anti-VAP device or an anti-VAP material in a region where secretions otherwise build up in the airway of the patient when intubated with the nasogastric tube and where these secretions may come from the esophagus.

BRIEF SUMMARY OF THE DRAWINGS

FIG. 2 shows a traditional endotracheal tube ETT with a pilot balloon for cuff inflation. The tube ETT is shown in relation to the supraglottic space 203, the distal trachea 205, and the subglottic space 200.

FIG. 15 shows an inventive anti-VAP system using a foam or sponge ball.

FIGS. 16 and 17 show respective top view 1700T and side view 1700S of ball 1700 of FIG. 15.

FIG. 18 shows a non-hydrated sample (left) 1800 next to a thinned sample (right) 1801.

DETAILED DESCRIPTION OF A PREFERRED EMBODIMENT OF THE INVENTION

Figure 1:
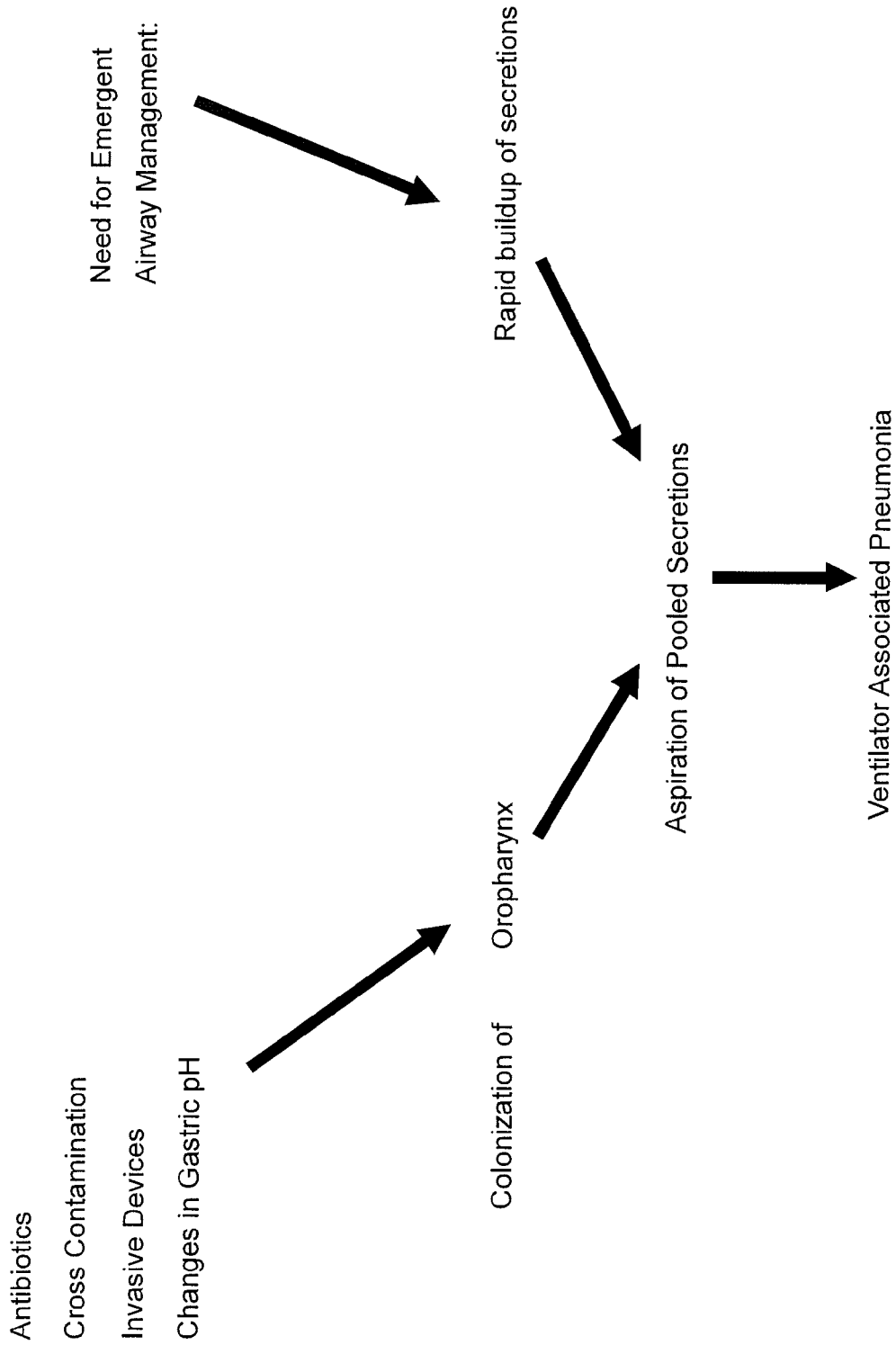
FIG. 1 is a chart showing a common pathway to development of VAP both early and late after intubation of a patient. The present invention is useful in both situations to reduce VAP.
Figure 2:
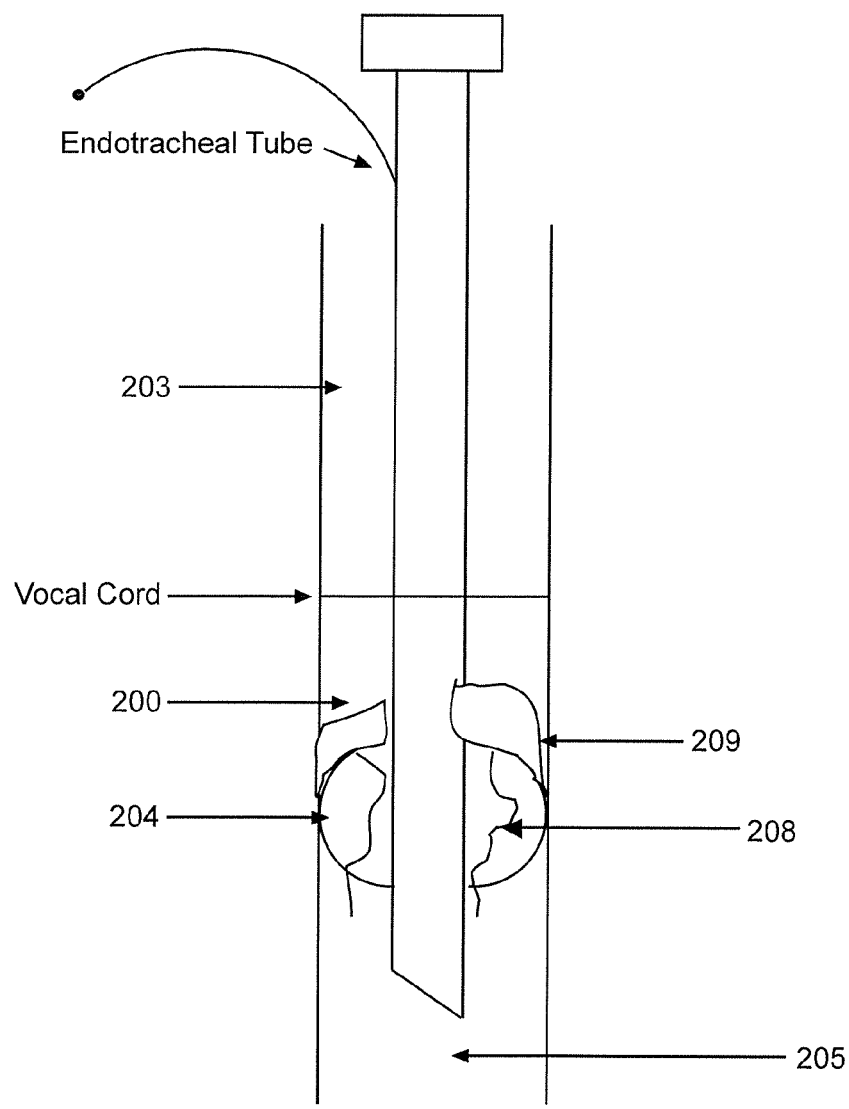
FIG. 2 is a cross-sectional view of pooled secretions in the subglottic space 200 (i.e., the space between inflated endotracheal balloon and vocal cords VC), which represents the problem when the invention is not in use.

The invention provides anti-VAP activity by controlling the space (namely, at and/or near (such as within about 1 cm of) the ETT of an intubated patient, such as space 208 in FIG. 2) where, if uncontrolled, VAP-causing agents otherwise accumulate and proceed to cause VAP. The accumulation of such secretions may be appreciated by referring to FIG. 2, which depicts (when the invention is not in use) pooled secretions in the subglottic space 200 (the space between the inflated endotracheal balloon and the vocal cords VC). This pooling results in microaspiration around the inflated endotracheal tube cuff 204 through small channels created between the cuff 204 and tracheal mucosa. Leakage 208 occurs of subglottic secretions through channels created from incomplete ETT balloon inflation. Such leakage 208 leads to VAP, as the present inventors have recognized.

In the invention, the space at and/or near the ETT (such as the space 209 of accumulating subglottic secretions in FIG. 2) is subjected to affirmative anti-VAP control, such as by occupying the space (such as by an anti-VAP device or an anti-VAP material (such as, e.g., a foam, liquid, gel, sponge, hydrogel, biomaterial, etc.)). For example, a space-occupying anti-VAP material or anti-VAP device is caused to occupy the space at and/or near the ETT, and the space-occupying material or device after a time is further controlled (such as by removing such a space-occupying anti-VAP material or anti-VAP device after a time). Subsequently, the space may be further controlled, such as by again causing the space to be re-occupied with an anti-VAP space-occupying material or device (which is not required to be the same as the removed anti-VAP material or device).

An anti-VAP material or anti-VAP device is not necessarily required to be treated or coated or to include an organism-killing agent. An anti-VAP material or anti-VAP device may, for example, merely provide a site for VAP-causing organisms to accumulate, with the site being removable from the patient before the accumulated VAP-causing organisms can cause VAP.

Examples of anti-VAP devices that may be used in an anti-VAP system include, e.g., attachments or adjuncts that can be added to any endotracheal tube before and in some cases after intubation, such as an anti-VAP device that is a sleeve. An anti-VAP device that is an attachment to an ETT advantageously removes problems of switching to a specific new endotracheal tube, and further increases the potential to reduce VAP by multiple and combined means, again without relying on the specifics of the underlying endotracheal tube used. An anti-VAP attachment to an ETT also advantageously allows for more flexibility as new materials and methods evolve in airway management including the prevention of VAP. An anti-VAP device may be disposable or may be reusable after treatment (such as sterilizing treatment).

An example of an anti-VAP device is a disposable sleeve. The disposable sleeve may be provided to surround the endotracheal tube balloon and/or more proximal sections of the tube.

Another example of an anti-VAP device is an elastic tubular member. When using the inventive elastic tubular member, there also may be practiced conventional strategies to reduce the potential for small longitudinal folds to occur upon endotracheal tube cuff inflation, such as, e.g., constructing the ETT balloon with other materials such as latex or silicone to reduce the formation of these channels or by eliminating the balloon altogether and replacing it with "gills". However, advantageously, the inventive elastic tubular member can be used with various endotracheal tubes and thereby the invention advantageously provides practical flexibility. An ETT may be placed through an inventive elastic tubular member that covers the native balloon and some portion of the distal and proximal ETT. This inventive tubular member could be made, e.g., of latex, silicone or other materials, which are coated or embedded with sliver or other bacteriocidal/static agents as well as anesthetics. These materials might be made in a manner or contain compounds inhibiting the formation of biofilms. The materials from which to form the inventive tubular members may be made to display various innate or induced electrostatic charges, which have been demonstrated to favorably affect inflammation and bacterial growth. The materials from which to form the inventive tubular members could allow for exogenous delivery (through ports in the sleeve) of antibacterial or anesthetic agents.

Anti-VAP devices and anti-VAP materials are not necessarily exclusive of each other. For example, an anti-VAP material may be formed into or used with an anti-VAP device. Importantly, the present invention is not limited to solids and non-solids may be used in practicing the inventive control of space where VAP-causing organisms otherwise accumulate. "Material" broadly includes any form, such as solids, liquids, foams, hydrogels, semi-solids, etc.

Example 1

Leakage Experiment

Experimentation regarding anti-VAP devices and/or anti-VAP materials was performed as follows.

7 mm ETT inflated in the barrel of 20 cc syringe, with dye leaking occurring around the cuff through channels formed between the cuff and the balloon: A photograph was taken that shows a screening methodology reported in other studies that uses the barrel of a 20 cc syringe to act as the trachea. It is intubated with an endotracheal tube followed by inflation of the cuff and introduction of dye above the balloon. A 7 mm ETT was used. Leakage of dye around the balloon can then be observed for. Leaking of dye is seen when the balloon is filled with 10 cc air.

7 mm ETT with rubber latex cover around the balloon, according to an embodiment of the invention: native balloon inflated: another photograph, another 7 mm ETT is used but before insertion into the "trachea" it was placed through a simple piece of a latex rubber drain. Inflation of the native balloon followed by instillation of dye was then performed. There is no evidence of leaking, even with manipulation of the proximal ETT. Identical results have been found using the finger portion of simple latex gloves. The tubular member may be constructed in such a manner that it comes with its own inflation port. Sleeves may be made with portions of the sleeve (which surround the ETT native balloon) expanding as the native balloon is inflated or these sleeves could contain their own balloon and inflation mechanisms. Inflation mechanisms may include, e.g., filling the sleeve balloon with self-expanding foam similar to that of the Bivona foam cuff product line. Again the sleeves may be coated with various materials or could have channels and ports allowing the delivery of various beneficial agents.

Example 2

Figure 3:
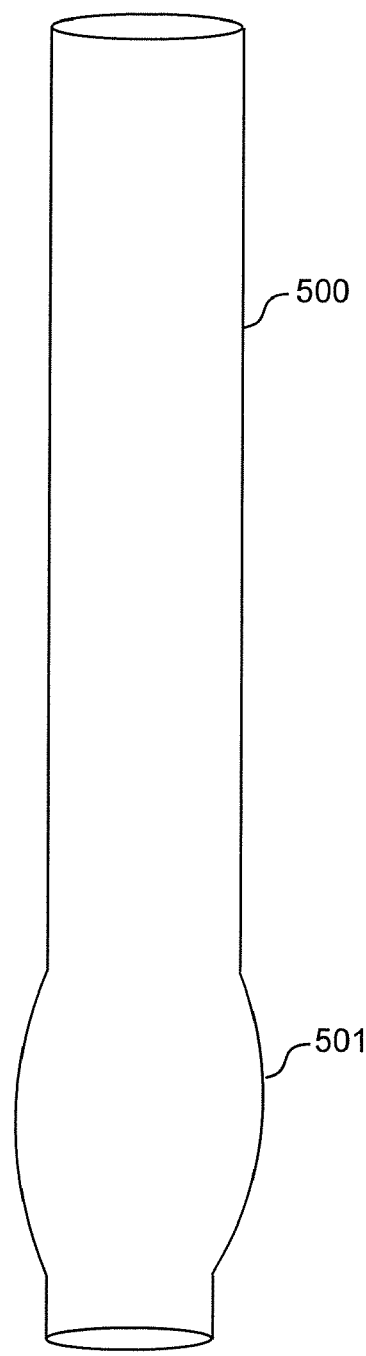
FIGS. 3 and 4 are cross-sectional views of an inventive open-ended sleeve through which an ETT is placed.

FIG. 3 shows an inventive open ended sleeve 500 or condom to be placed over an ETT prior to intubation. A portion 501 of the sleeve 500 goes over the ETT balloon and expands as the balloon expands.

Modification of the end of the sleeve 500 allows for the native balloon to be covered with a material that would not lead to formation of channels between the ETT attachment and the tracheal mucosa when the native balloon is inflated. The sleeve 500 may be embedded with antimicrobials/bacteriostatic agents and anaesthetics. Materials used for forming the sleeve 500 preferably are resistant to formation of biofilms.

Figure 4:
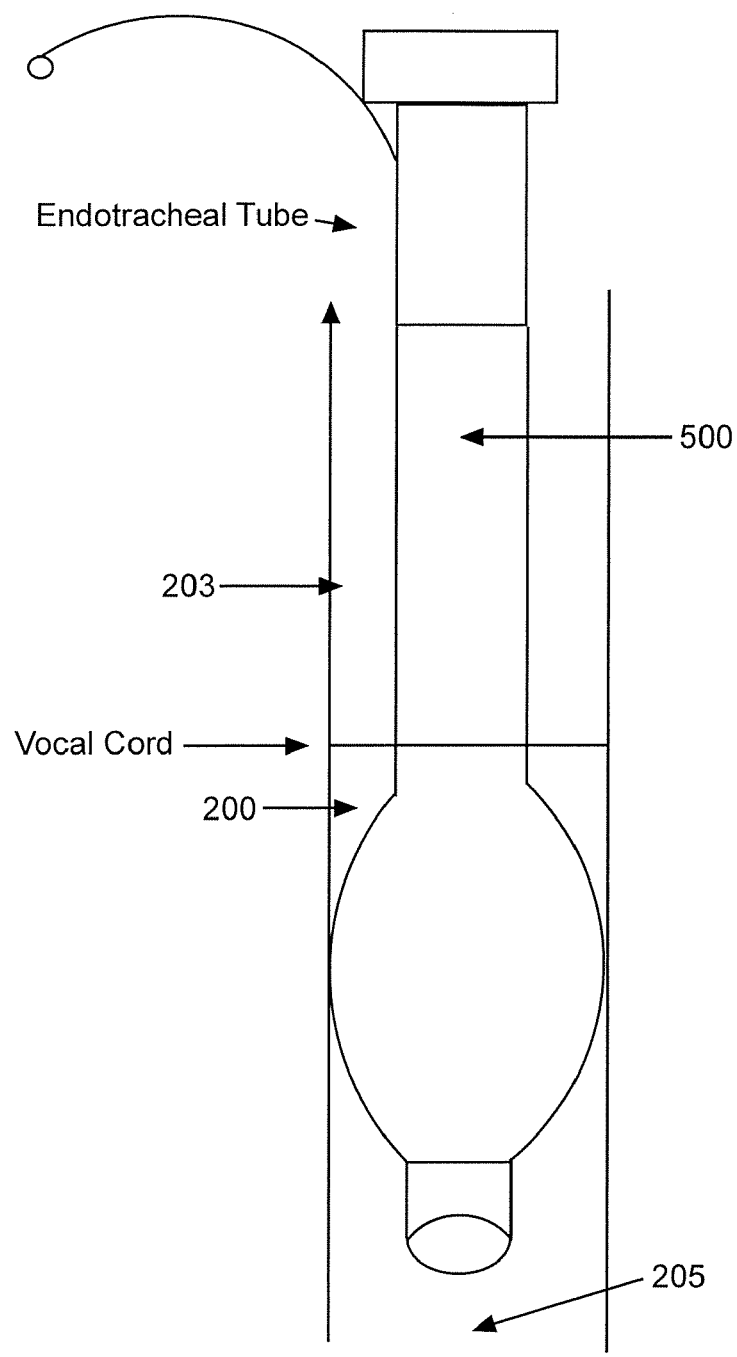

FIG. 4 shows the inventive sleeve 500 extending from below the balloon to the proximal tube when the sleeve 500 is used with a traditional endotracheal tube ETT with a pilot balloon for cuff inflation. The endotracheal tube ETT, supraglottic space 203, vocal cords VC, and subglottic space 200 in FIG. 4 are as in FIG. 2. The sleeve 500 optionally may have a separate inflation port (not shown) for the balloon cover portion.

Example 2A

Figure 5:
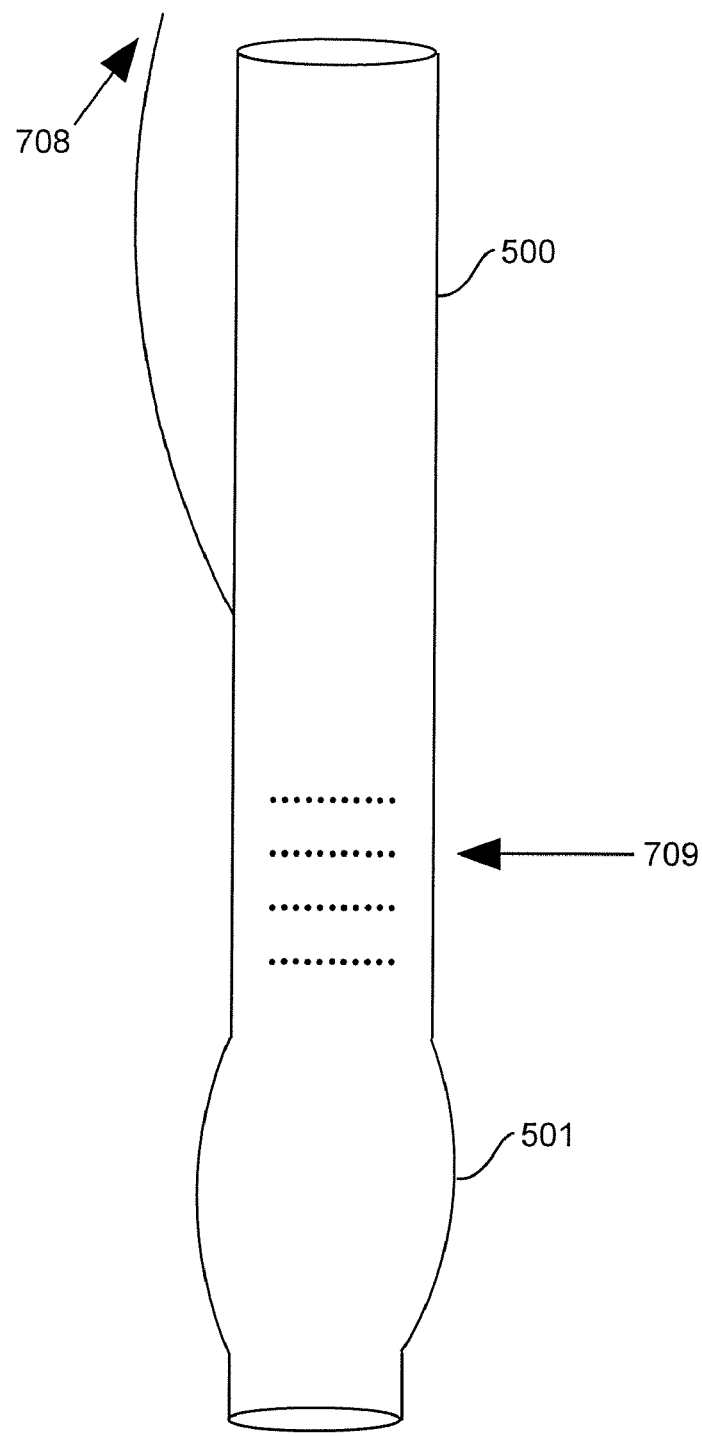
FIG. 5 is a cross-sectional view of the sleeve of FIG. 5 modified to include ports for delivery of compounds such as antimicrobials and anesthetics.

FIG. 5 is a modified version of the sleeve 500 of FIG. 3, modified to include ports 709 for delivery of compounds (such as antimicrobials, anesthetics, etc.) and port 708 for injection of compounds (such as anesthetics, antimicrobials, etc.).

Example 2B

Figure 7:
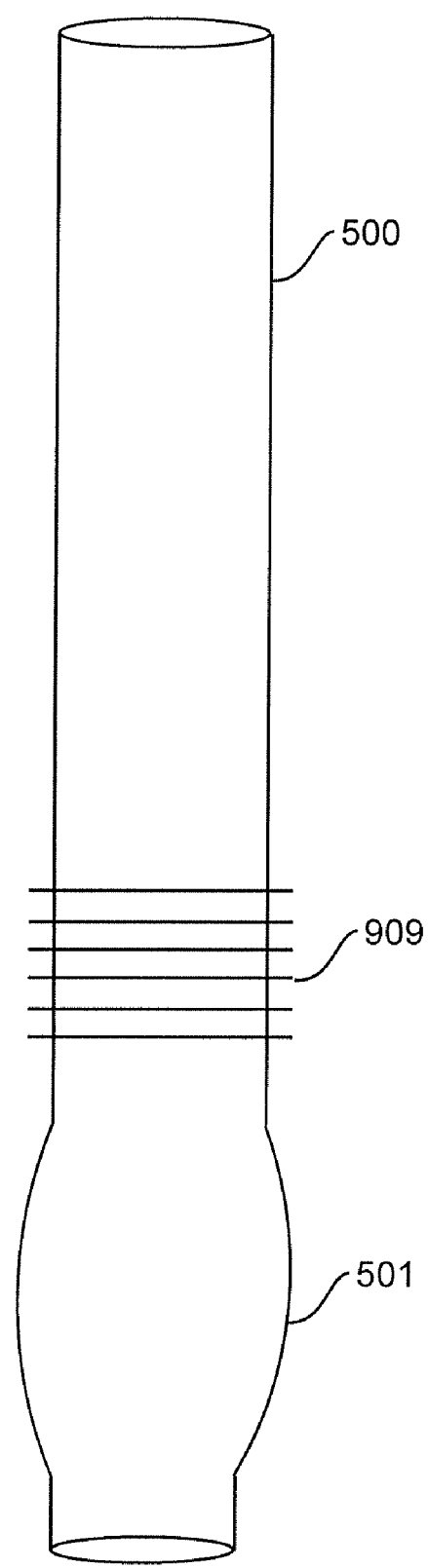
FIG. 7 shows an inventive sleeve in which conventional barrier strategies such as gills additionally may be used.

The inventive sleeves may have conventional barrier technology such as "gills" (e.g., Reali-Forster, supra.) attached to them. For example, a sleeve 500 (of FIG. 3) may have gills 909 added as shown in FIG. 7, to increase the barrier function of the sleeve 500.

Example 3

Figure 6:
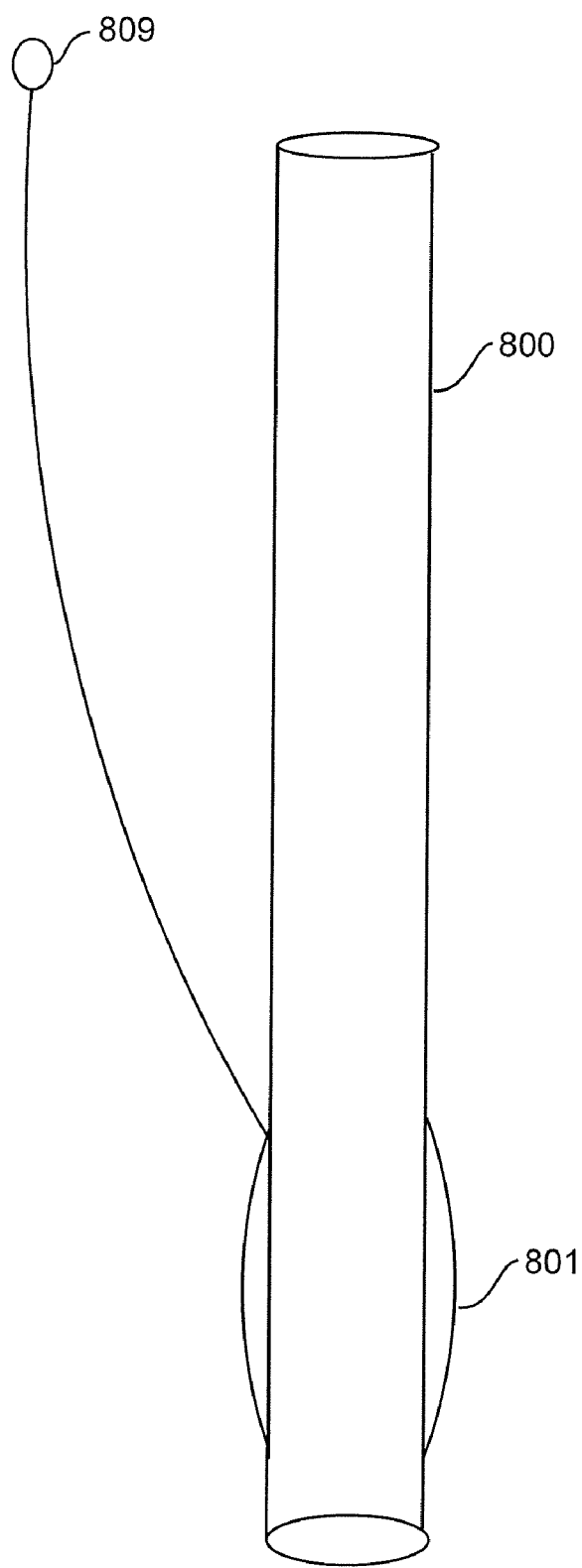
FIG. 6 shows an inventive sleeve containing its own balloon and inflation mechanisms.

Referring to FIG. 6, the inventive sleeve 800 (which may contain special compounds) contains its own balloon 801 (which may be made of, e.g., silicone, latex, or other material resistant to the formation of channels) and inflation mechanisms. The open-ended sleeve 800 or condom is placed over the ETT prior to intubation. The sleeve 800 contains its own balloon 801 expanded with air or containing foam which self-expands. Pilot balloon and stem 809 for inflation of the sleeve balloon are shown in FIG. 6. The sleeve balloon 801 also may contain foam sponge similar to Bivona strategy and foam sponge deflated by aspiration, and then inflated when exposed to atmospheric pressure. The stem 809 is then attached in line to a ventilator circuit. That is, the ports of the balloons 801 are hooked in line with the ventilator circuit so that additional expansion takes place during mechanical ventilation. The balloons 801 may be coated with antimicrobials and anesthetics.

Example 4

An anti-VAP attachments may include, e.g., a sleeve containing a suction and/or delivery port so that subglottic secretions could be suctioned. Alternatively, the subglottic space could be obliterated by injecting various water-soluble hydrogels or foaming agents containing bacteriostatic and anesthetic properties to act as a barrier and to bathe the mucosa and vocal cords. This could be exchanged daily by suctioning and then injecting new material. Agents conventionally used for wound care may be applied.

Figure 8:
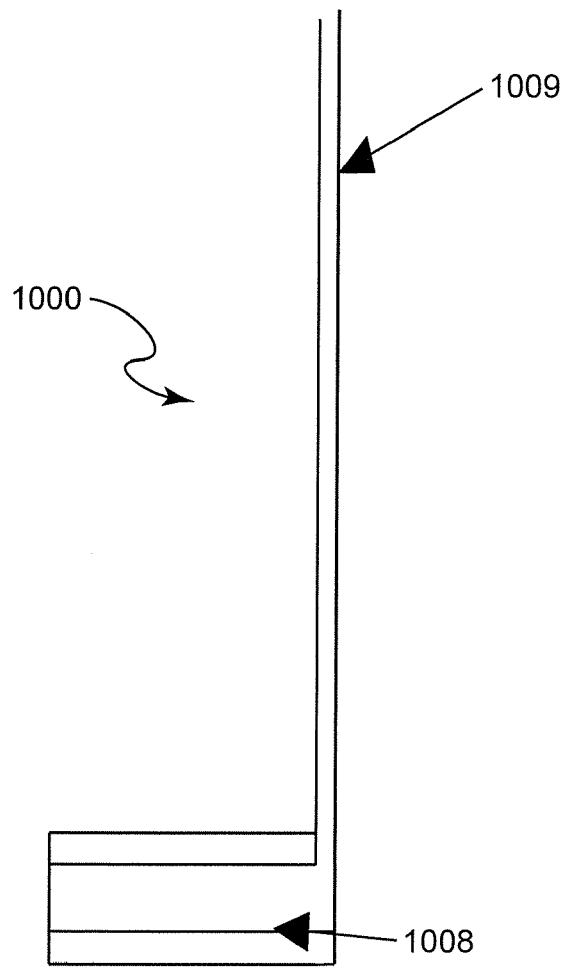
FIGS. 8 and 9 are views of an inventive anti-VAP attachment that allows for suctioning of the subglottic space or delivery of hydrogels or other compounds to the subglottic space to obliterate the space and act as an additional barrier.

In FIG. 8, a suctioning ring attachment 1000 is shown, that may be placed around an ETT either before or after patient intubation. Port 1009 in FIG. 8 is a suctioning port or delivery port. The inventive sleeve in FIG. 8 includes a near circumferential opening 1008 of the ring connecting to the port 1009 for suctioning or delivery of hydrogel barrier or other materials.

Example 4A

Figure 9:
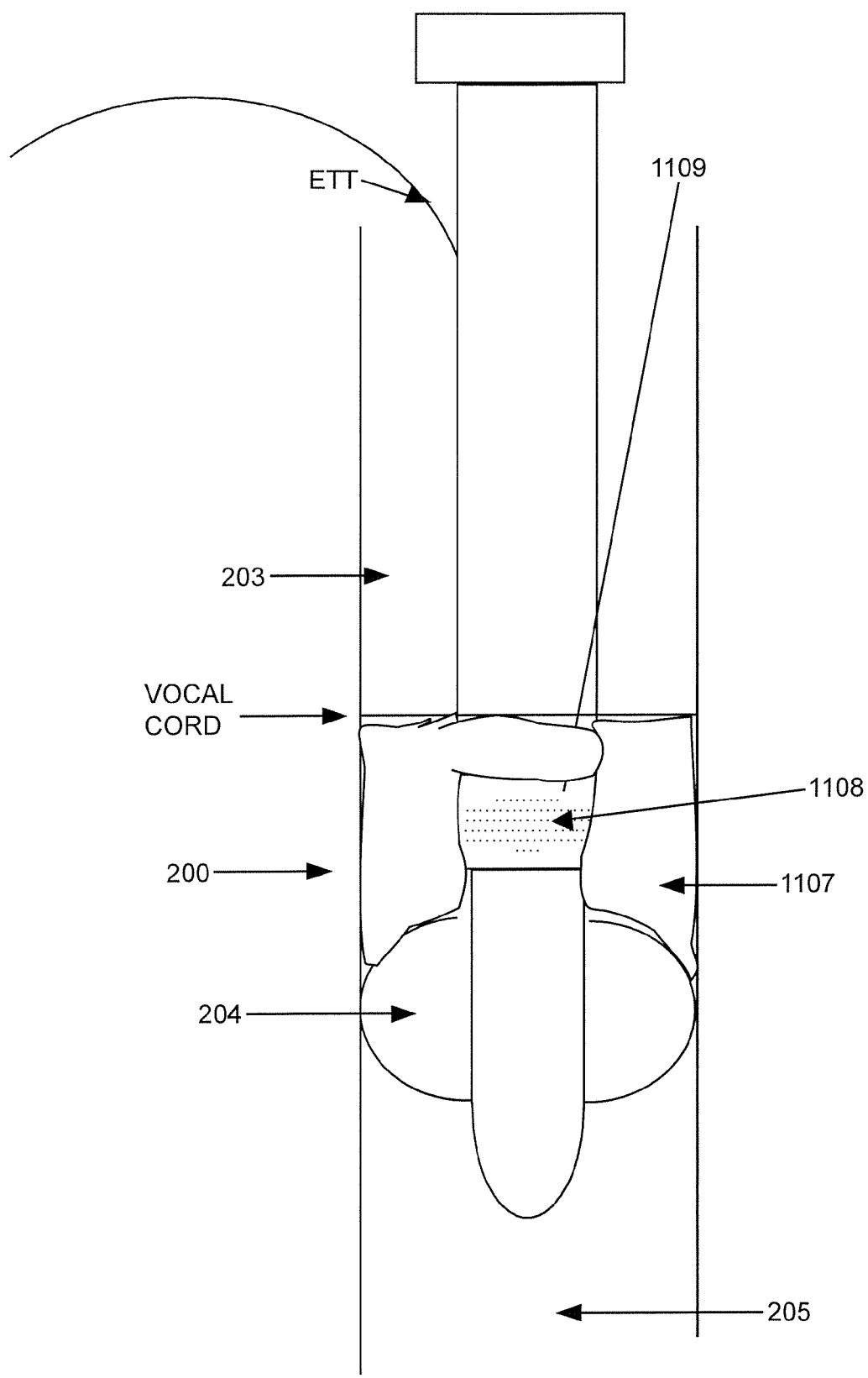

FIG. 9 shows another inventive port-containing sleeve, shown after intubation of the ETT. As in earlier figures, the following are comparably numbered: the endotracheal tube ETT which may be a traditional endotracheal tube, the supraglottic space 203, the vocal cords VC, the subglottic space 200, the inflated endotracheal tube cuff 204 and distal trachea 205.

In FIG. 9, sleeve port 1109 is for injection of additional hydrogel to fill both supraglottic and subglottic space. The port 1109 may also contain conductive materials to produce various charges around the sleeve.

The ETT sleeve has ports 1108 to allow for extrusion of hydrogel into the supraglottic space 203 and subglottic space 200. Injected hydrogel (or other material) 1107 obliterates subglottic space 200 providing a barrier function and delivery of antimicrobial, anesthetic, and other compounds.

Example 5

Figure 10:
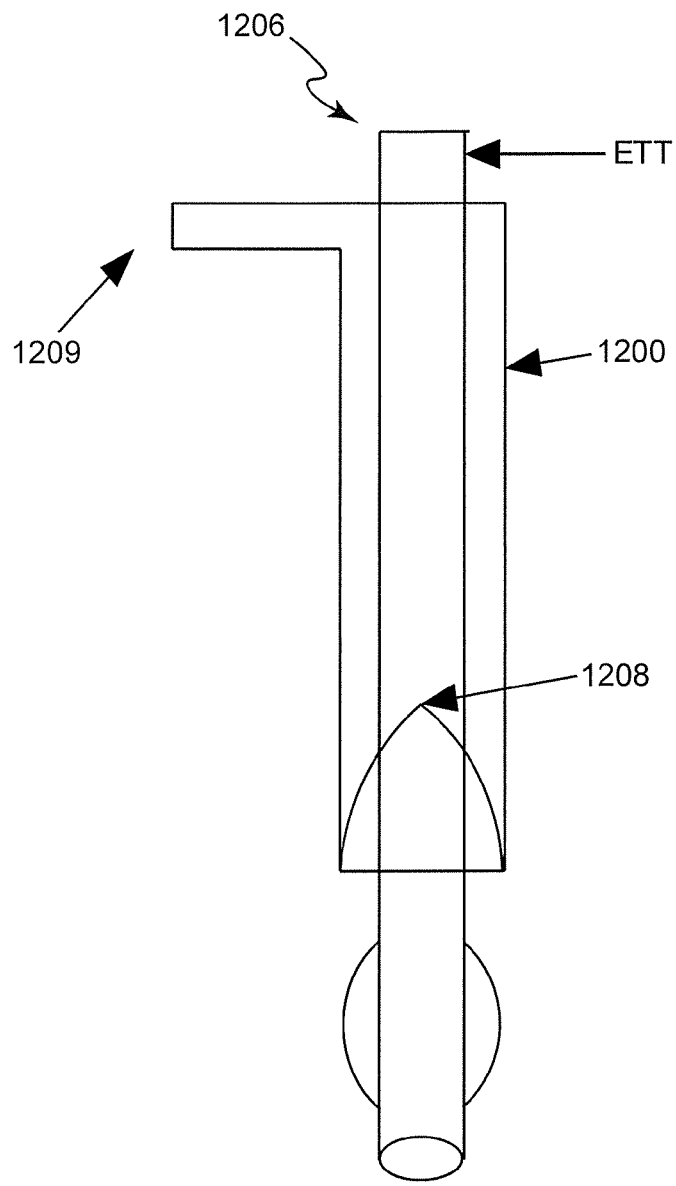
FIG. 10 shows an inventive sleeve ETT attachment that isolates the supraglottic area preventing passage of secretions to the subglottic space.

As seen with reference to FIG. 10, another example of an inventive anti-VAP attachment to a tube ETT is a sleeve 1200 allowing isolation of the supraglottic area similar to that of the laryngeal mask airway. The device of FIG. 10 includes a flexible covering 1206 allowing delivery of aerosolized or other forms of anesthetics or antimicrobials to the supra and subglottic areas. Optionally, the device may be modified to allow for suction and could be formed to fit over or surround the epiglottis similar to a laryngeal mask airway.

Sleeve part 1208 is a covering that may fit over the epiglottis/supraglottic area similar to a laryngeal mask airway. Optionally an inflatable balloon may be used to make the seal around the supraglottic area.

The sleeve 1200 may contain antimicrobials and anesthetics. Suctioning may take place through this anti-VAP device. In addition, this anti-VAP device may allow for delivery of agents to the supra and immediate subglottic area such as anesthetic or antibacterial aerosols. Port 1209 is for introduction of compounds (such as aerosolized compounds, antimicrobials, anesthetics, etc.) to the supraglottic and subglottic space, or suctioning.

Again, as mentioned for other anti-VAP sleeves, this anti-VAP sleeve may be coated with or contain antimicrobials, bacteriocidal and anesthetic agents, etc.

An example of a prototype that was made and photographed is a thinned product bent into an inventive circular sleeve with the ends sutured together, then the inventive sleeve was placed over an endotracheal tube.

Example 6

The invention also provides anti-VAP foam/sponge sleeves (such as wound foams/sponges which contain dyes and other material which can be bacteriostatic) that may be attached and then activated causing them to swell to obliterate the subglottic space. The foam absorbs secretions and increases contact time of bacteria with a bactericidal agent used in or with the foam. The foam may traverse the vocal cords.

Referring to FIGS. 11-14, ETT attachments (such as the foam/hydrogel sleeve 1300 in FIG. 11) which may be made of foam are shown. Foam ETT attachments expand when placed into contact with moisture. The foam may be embedded with antimicrobials or anesthetics. The sleeves shown in FIGS. 11-14 show a strategy in which a barrier function and drug delivery are provided.

Figure 11:
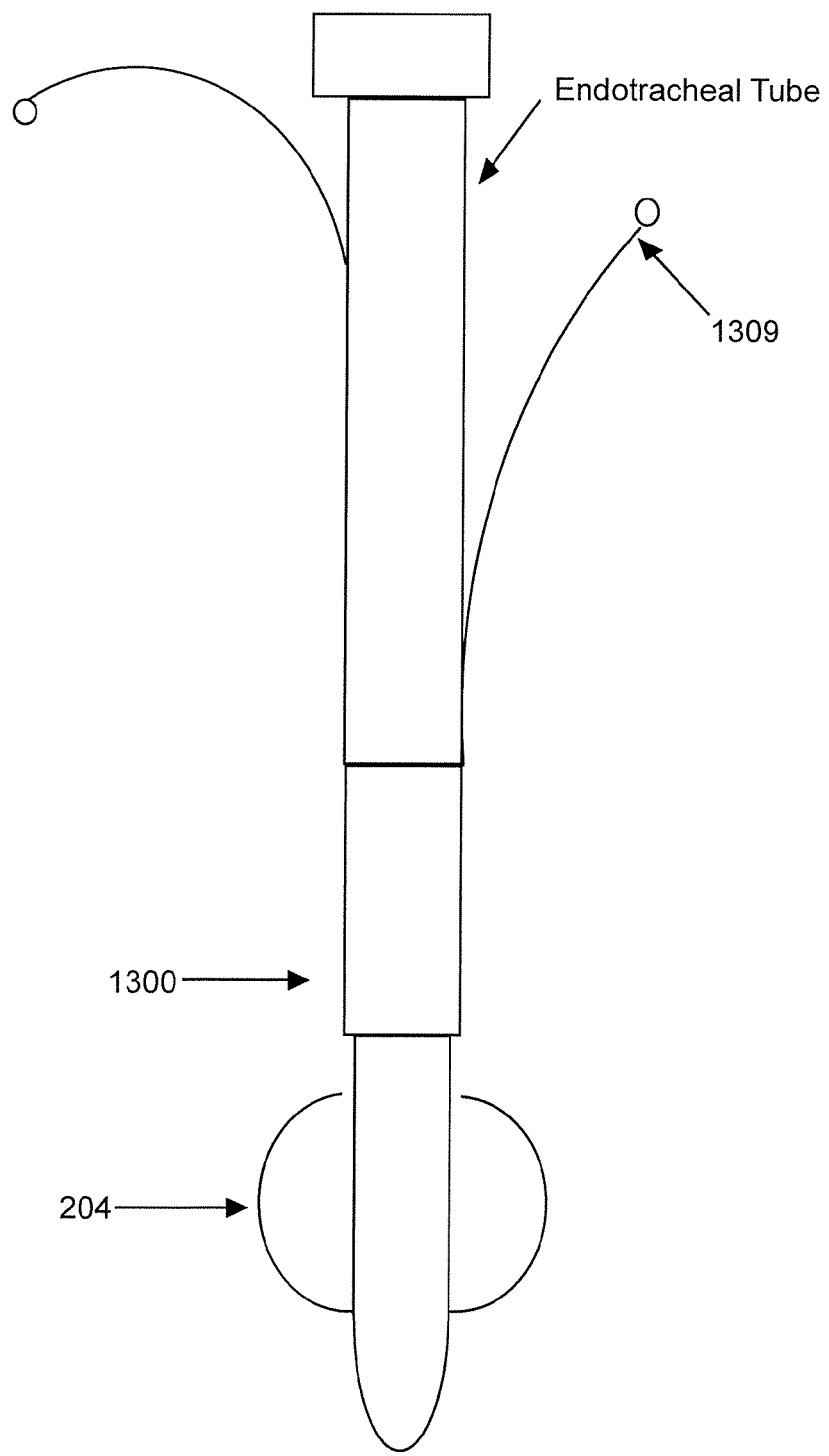
FIGS. 11-14 show inventive anti-VAP foam ETT attachments.

In FIG. 11, an endotracheal tube ETT wearing a foam/hydrogel sleeve 1300 is shown prior to intubation. Through a hydrogel sleeve port 1309, there may be injected water, additional hydrogel, or other activating agents. FIG. 11 shows a non-hydrated status of the sleeve 1300.

Figure 12:
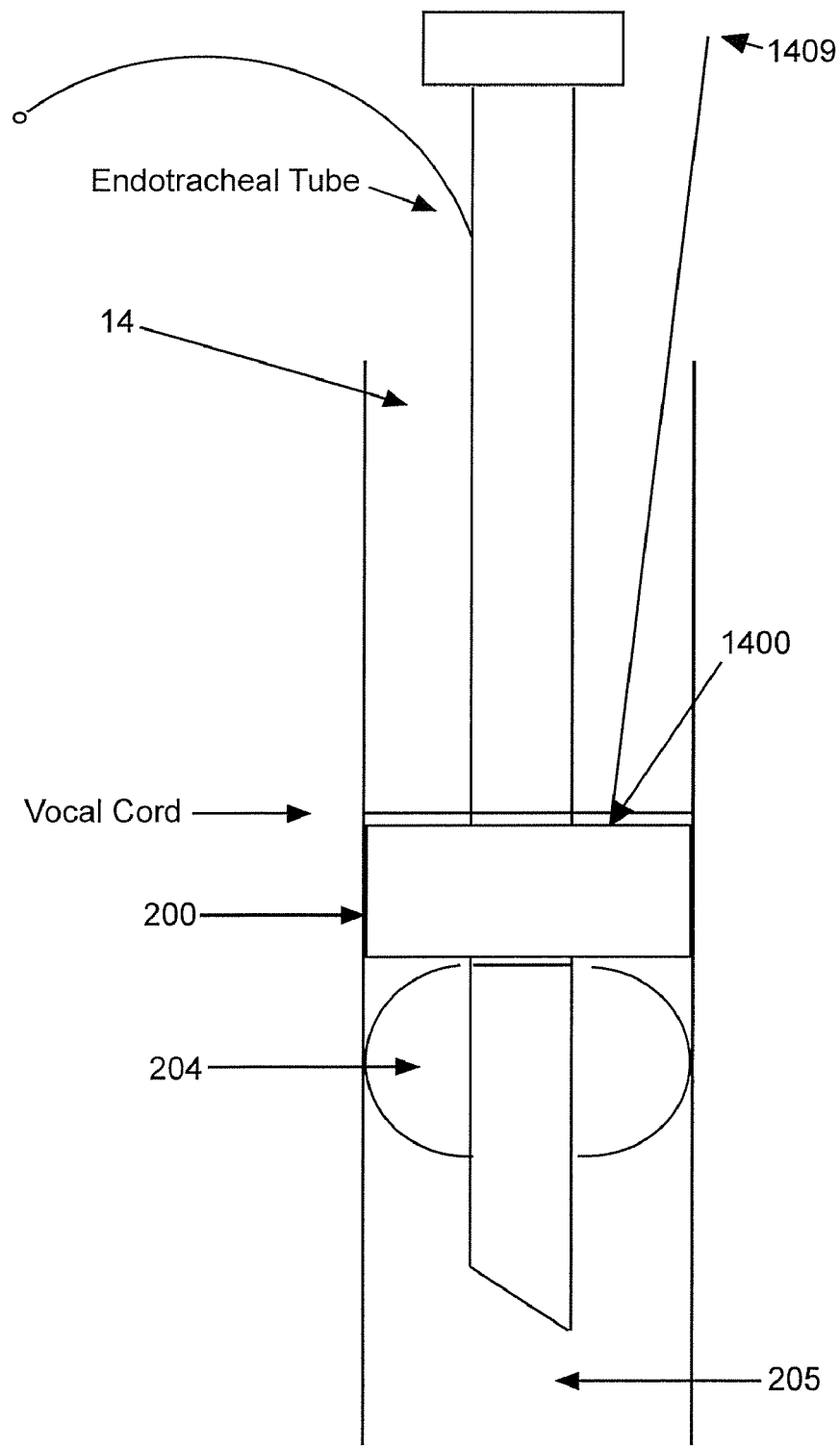

In FIG. 12, a medical foam material sleeve 1400 assembled on an ETT is activated to an expanded state below the trachea 14. A stem 1409 is provided to the sleeve 1400 allowing hydration.

Figure 13:
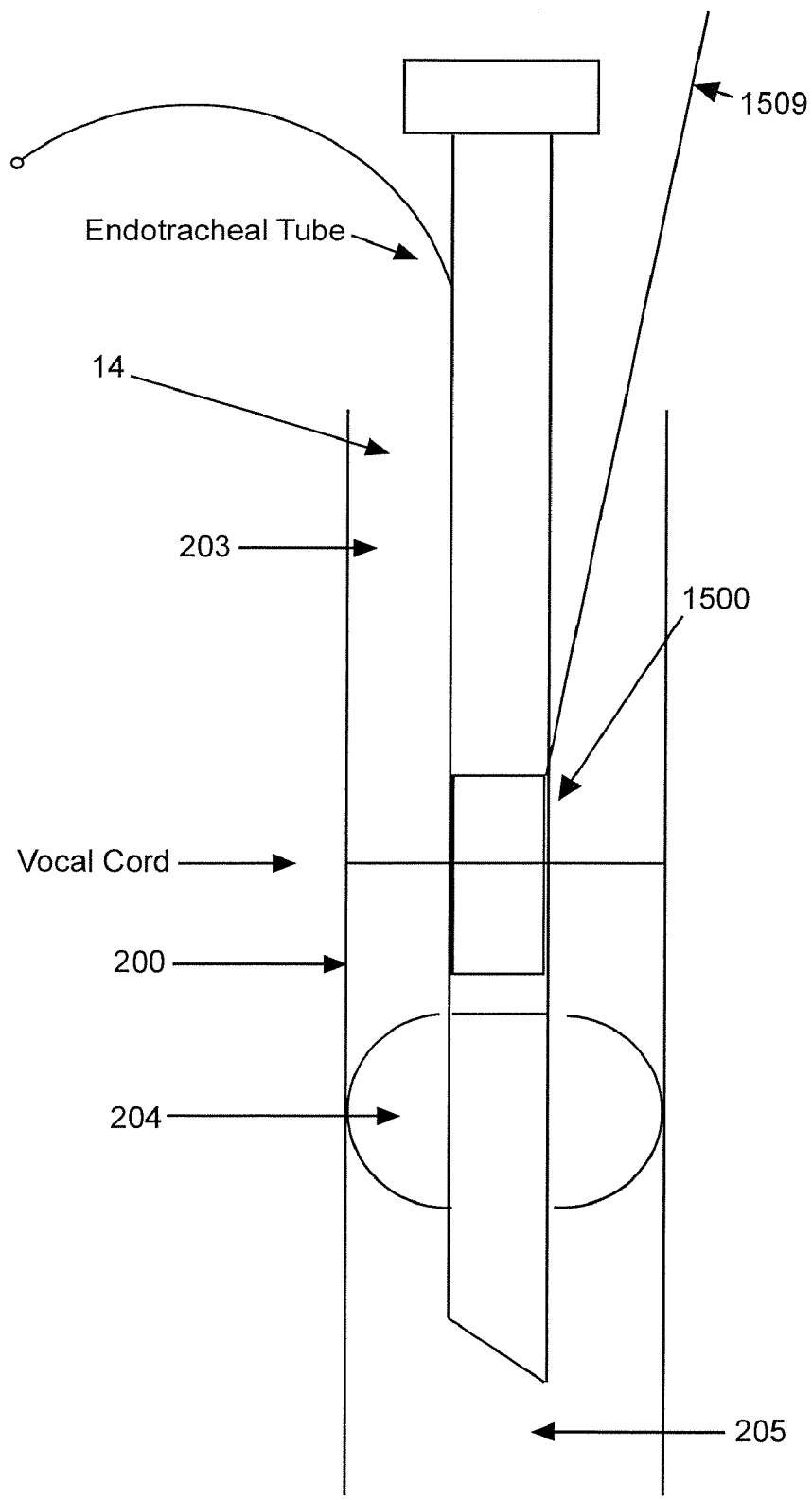

In FIG. 13, a sleeve 1500 (such as a sleeve comprising hydrogel, non-hydrated medical foam, or another material) is assembled on an ETT, in an unactivated state, and spanning the vocal cords VC. A stem 1509 to the sleeve 1500 permits hydration.

Figure 14:
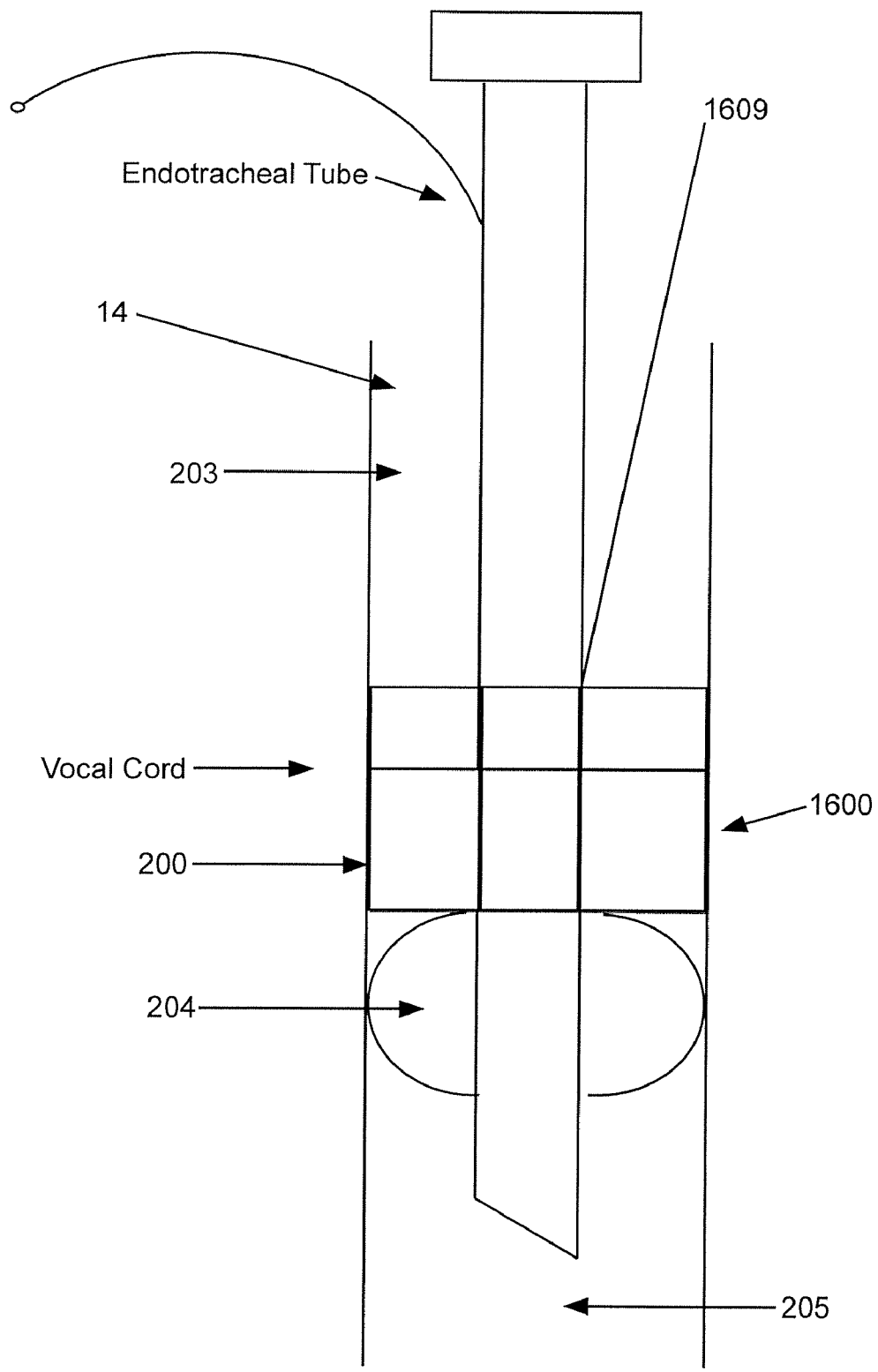
Figure 18A:
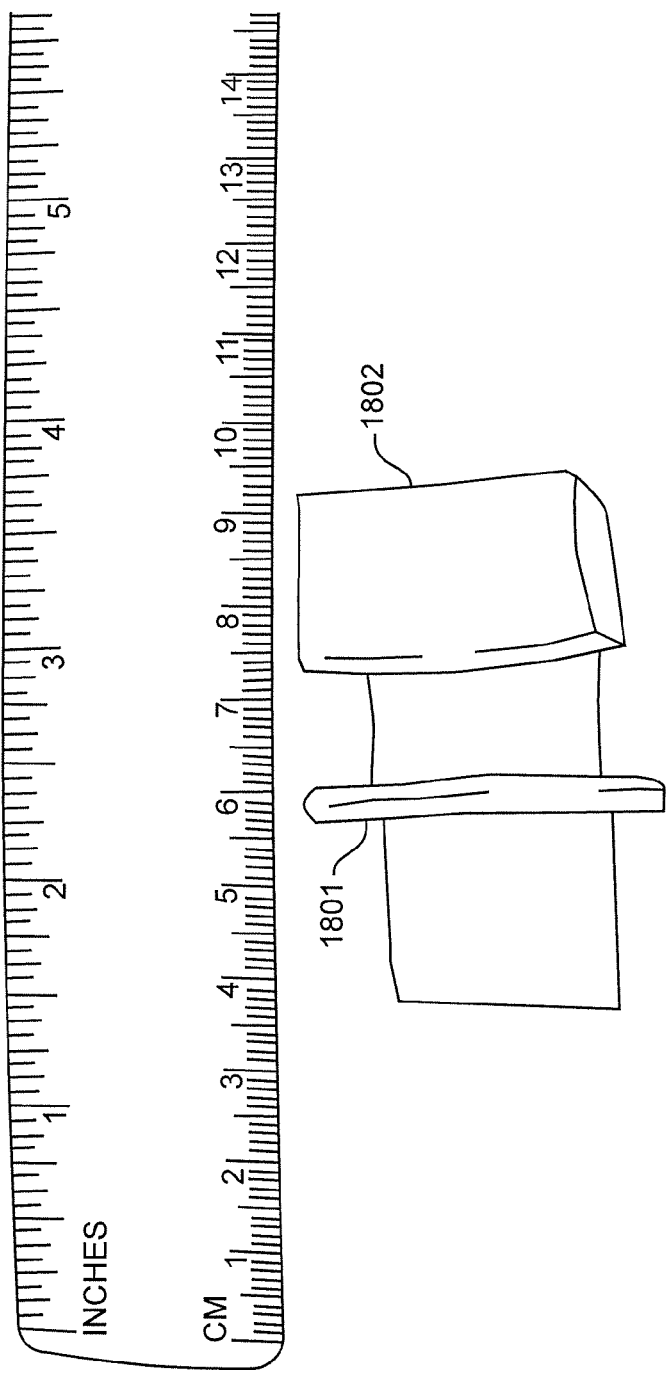
FIG. 18A shows a thinned sample (left) 1801 next to a hydrated thinned sample (right) 1802.
Figure 18B:
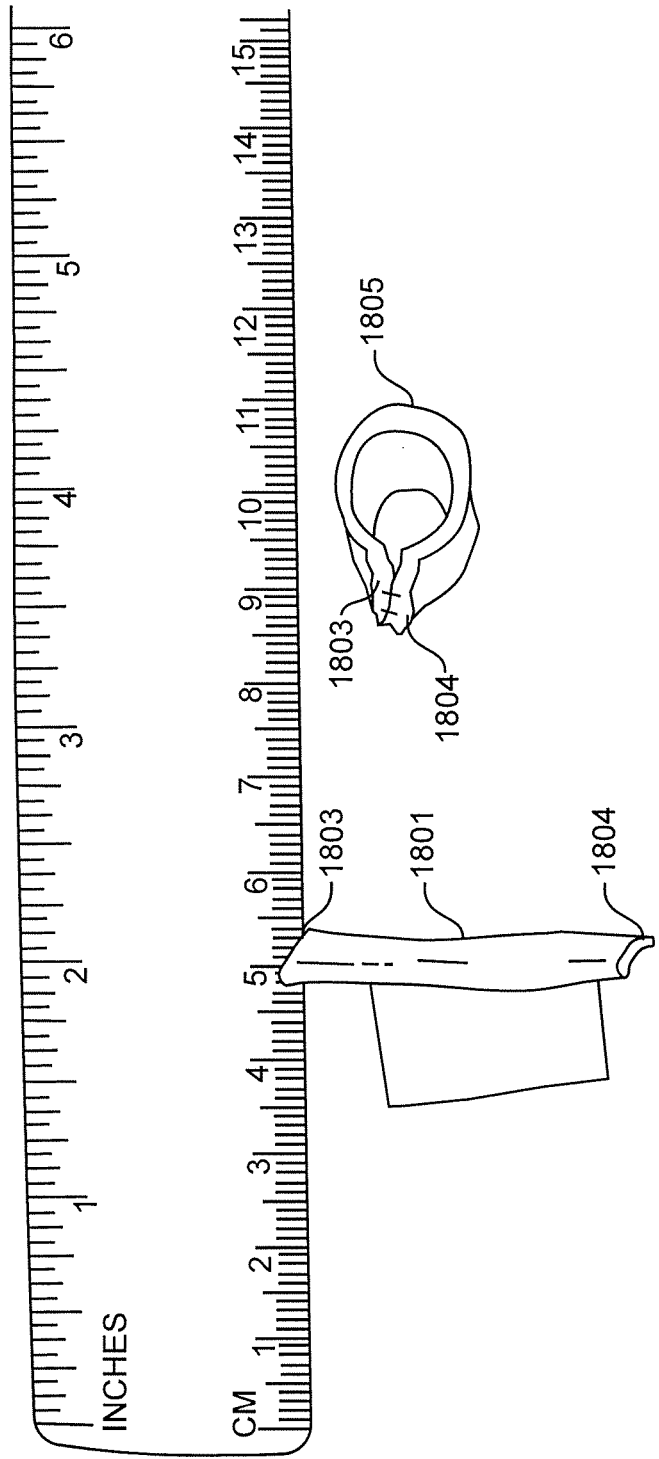
FIG. 18B shows a thinned product (left) 1801 with ends 1803, 1804 bent into an inventive circular sleeve (right) 1805 with the ends 1803, 1804 sutured together.
Figure 18C:
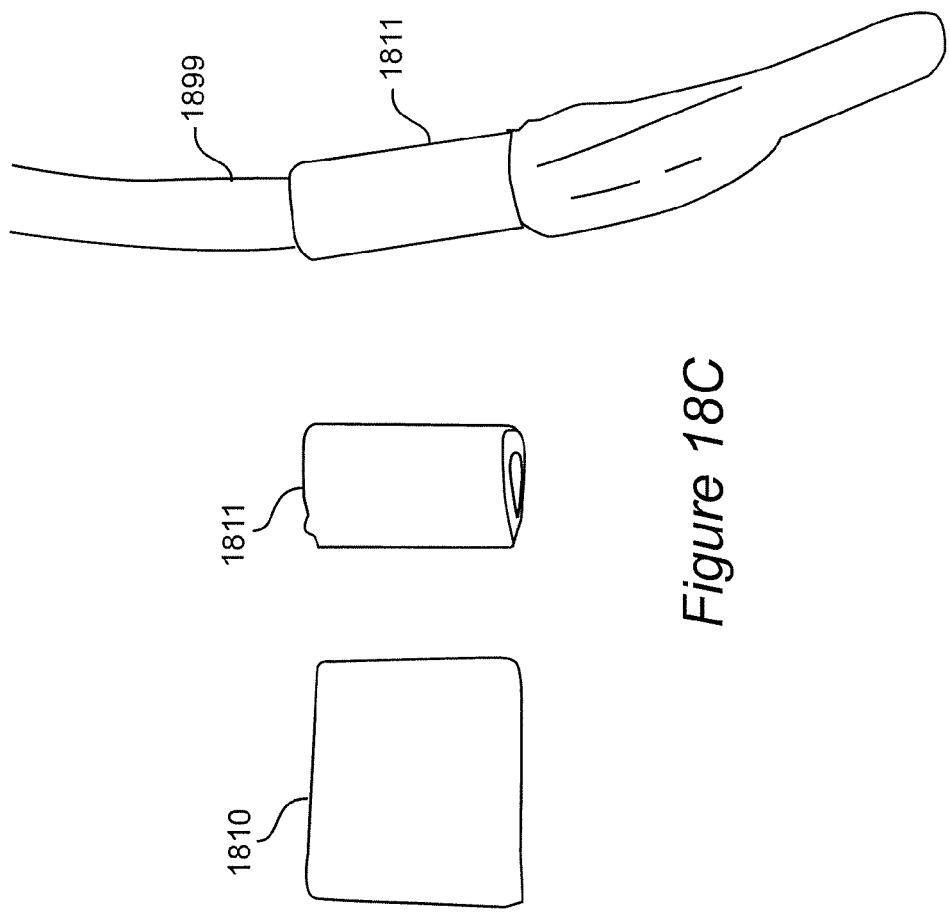
FIG. 18C'shows a thinned sample (left) 1810 made into an inventive sleeve (middle) 1811, with the inventive sleeve 1811 placed over an endotracheal tube (right).

In FIG. 14, an activated sleeve 1600 (such as a hydrogel sleeve) is shown spanning the vocal cords VC, and expanding to consume most of the subglottic space forming an impenetrable barrier. A stem 1609 to the sleeve 1600 permits hydration. The hydrate foam or other material of the sleeve 1600 spans through the vocal cords VC essentially eliminating the subglottic space.

Example 7

A foam/sponge ball or other shaped member (sleeve) with a hollow core may be placed around the ETT. This ball or sponge sleeve may be gently compressed and slid far down into the supraglottic area of the oropharynx where it acts act as a super absorber of secretions. The foam may be embedded with antimicrobials of various sorts and optionally may contain and anesthetic. It may be nonadherent and thus friendly to the epiglottis. The foam ball, sleeve, or ring may be replaced at regular intervals.

Referring to FIG. 15, a foam/sponge ball 1700 is shown, but alternately a non-ball shape may be used, preferably a shape that conforms to the entire posterior pharynx. Ball 1700T is the top view and ball 1700S is the side view of the oropharyngeal foam ball 1700. The ball 1700 acts as a secretion barrier and absorbs secretions. The ball 1700 may be loaded with anesthetics and/or antimicrobials/bacteriostatic agents. The ball 1700 is removable and replaceable.

Example 8

The invention may be applied to nasogastric tubes (esophageal and oropharyngeal portions), to reduce aerodigestive colonization to which nasogastric tubes otherwise contribute. Anti-infection devices and anti-infection materials (such as, e.g., removable, disposable anti-infection devices and anti-infection materials) may be used to control the space within a patient intubated with a nasogastric tube in the space where otherwise infection-causing organisms would accumulate.

The inventive devices, materials, systems and methods discussed herein with references to the Figures are especially preferred for use with human patients but also is useful in veterinary embodiments. In an example of using the invention during intubation, by comparison to a standard endotracheal tube that passes through the vocal cords, an inventive non-hydrated sleeved endotracheal tube passes through the vocal cords and into the trachea, with the sleeve spanning the vocal cords. In another example of using the invention, an inventive hydrated sleeve is on an endotracheal tube, with the sleeve spanning the vocal cords.

In practicing the invention, one or more inventive anti-VAP device(s) may be used alone, or with one or more anti-VAP material(s). The inventive anti-VAP methods, systems and devices may be used to reduce microaspiration, reduce oropharyngeal bacterial load, and/or to provide airway anesthesia.

In the inventive methods and in using the inventive devices and systems, optionally suctioning may be performed. For example, an anti-VAP device may be used that allows suctioning from around close proximity of the ETT (such as above the ETT balloon).

While the invention has been described in terms of its preferred embodiments, those skilled in the art will recognize that the invention can be practiced with modification within the spirit and scope of the appended claims.

What we claim as our invention is:

1. A method of reducing occurrence of ventilator associated pneumonia (VAP) in a patient whose esophagus is intubated with a nasogastric tube, comprising:
    disposing an anti-YAP sponge device or an anti-VAP spongy material in a region where secretions otherwise build up in the airway of the patient when intubated with the nasogastric tube and when these secretions may come from the esophagus.

2. A method of preventing ventilator associated infection in a patient intubated with a cuffed tube that is an endotracheal tube that includes a cuff, comprising:
    within the intubated patient, non-surgically disposing a controllably-removable anti-infection device or an anti-infection material in an open space external to the cuffed tube and where otherwise infection-causing organisms and secretions would accumulate, and wherein the anti-infection device or anti-infection material is other than the cuff or the cuffed tube;
    wherein the disposing step includes disposing an anti-VAP device comprising a sponge or an anti-VAP spongy material;
    preventing leakage of subglottic secretions wherein the anti-infection device or the anti-infection material performs the leakage-preventing;
    removing the anti-infection device or anti-infection material from the intubated patient while the cuffed tube remains in the patient during the removing step;
    wherein the patient is intubated with an ETT having an inflated balloon where channels may form between the cuff and tracheal mucosa from incomplete ETT balloon inflation, and the method includes preventing leakage of subglottic secretions through said channels.

3. A method of preventing ventilator associated infection in a patient intubated with a cuffed tube that is an endotracheal tube that includes a cuff, comprising:
    within the intubated patient, non-surgically disposing a controllably-removable anti-infection device or an anti-infection material in an open space external to the cuffed tube and where otherwise infection-causing organisms and secretions would accumulate, and wherein the anti-infection device or anti-infection material is other than the cuff or the cuffed tube;

in which the disposing step is a step of disposing a controllably-removable anti-infection device;

preventing leakage of subglottic secretions wherein the anti-infection device or the anti-infection material performs the leakage-preventing;

removing the anti-infection device or anti-infection material from the intubated patient while the cuffed tube remains in the patient during the removing step;

wherein the patient is intubated with an ETT having an inflated balloon where channels may form between the cuff and tracheal mucosa from incomplete ETT balloon inflation, and the method includes preventing leakage of subglottic secretions through said channels.

4. The method of claim 3, wherein the infection is VAP.

5. The method of claim 3, wherein the patient is selected from the group consisting of: a human patient and a veterinary patient.

6. The method of claim 3, further including a step of providing airway anesthesia while the disposing step is performed.

7. The method of claim 3, wherein the material or device provides a site for VAP-causing secretions and organisms to accumulate, the method including a step of removing the site from the patient before the accumulated VAP-causing secretions and organisms can cause VAP.

8. The method of claim 3, including operating a port through which to extrude a hydrogel into a subglottic space and extruding the hydrogel into a form of a barrier.

9. The method of claim 3, including performing the removing step after the device or material has occupied the space for at least one hour.

10. The method of claim 3, wherein the leakage preventing step includes preventing accumulation of subglottic secretions.

11. The method of claim 3, wherein the anti-infection device or material is macroscopic-sized.

12. A method of preventing ventilator associated infection in a patient intubated with a cuffed tube that is an endotracheal tube that includes a cuff, comprising:

within the intubated patient, non-surgically disposing a controllably-removable anti-infection device or an anti-infection material in an open space external to the cuffed tube and where otherwise infection-causing organisms and secretions would accumulate, and wherein the anti-infection device or anti-infection material is other than the cuff or the cuffed tube;

including disposing an anti-infection device or an anti-infection material shaped as a circular sleeve;

preventing leakage of subglottic secretions wherein the anti-infection device or the anti-infection material performs the leakage-preventing;

removing the anti-infection device or anti-infection material from the intubated patient while the cuffed tube remains in the patient during the removing step;

wherein the patient is intubated with an ETT having an inflated balloon where channels may form between the cuff and tracheal mucosa from incomplete ETT balloon inflation, and the method includes preventing leakage of subglottic secretions through said channels.

13. A device that accumulates infection-causing organisms for removal from a patient having a subglottic space and an entire posterior pharynx, the device comprising:

a member comprising a sponge or a spongy material, the member shaped to conform to the entire posterior pharynx wherein when the device is in the patient, the device, which is an impenetrable barrier, accumulates secretion-containing infection-causing organisms.

14. The device of claim 13, consisting of the sponge or the spongy material.

15. The device of claim 13, including a hollow core within the member whereby the member attaches around an exterior surface of an endotracheal tube or a nasogastric tube, the member being detachable therefrom.

16. The device of claim 13, wherein the device is removable from an intubated patient having a tube therein while the tube remains in the patient.

17. The device of claim 13, wherein when the device is in the patient, the device accumulates VAP-causing secretions and organisms.

18. The device of claim 13, wherein the device is non-surgically disposable into and removable from the patient while an ETT is in the patient.

19. The device of claim 13, wherein the device swells and obliterates the subglottic space of the patient.

20. The device of claim 13, having a shape that conforms to the entire posterior pharynx.

21. The device of claim 13, wherein the impenetrable barrier is macroscopic-sized.

22. A device that accumulates secretions and infection-causing organisms for removal from a patient having a subglottic space and an entire posterior pharynx, the device comprising:

a circular sleeve, the circular sleeve configured to receive therein an exterior surface of an endotracheal tube or a nasogastric tube, the circular sleeve being detachable therefrom; wherein the circular sleeve before use in the patient is thinned and when used in the patient becomes hydrated and expanded.

* * * * *